(12) United States Patent
Perschbacher et al.

(10) Patent No.: US 8,055,341 B2
(45) Date of Patent: Nov. 8, 2011

(54) BACKUP PACING DURING TACHYCARDIA

(75) Inventors: David L. Perschbacher, Coon Rapids, MN (US); James O. Gilkerson, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 360 days.

(21) Appl. No.: 12/326,517

(22) Filed: Dec. 2, 2008

(65) Prior Publication Data

US 2009/0157135 A1 Jun. 18, 2009

Related U.S. Application Data

(60) Provisional application No. 61/007,458, filed on Dec. 12, 2007.

(51) Int. Cl.
*A61N 1/00* (2006.01)
(52) U.S. Cl. .......................................................... 607/14
(58) Field of Classification Search ...................... 607/14
See application file for complete search history.

(56) References Cited

U.S. PATENT DOCUMENTS

| | | | |
|---|---|---|---|
| 4,875,483 A | 10/1989 | Vollmann | |
| 4,880,005 A | 11/1989 | Pless et al. | |
| 5,928,271 A | 7/1999 | Hess et al. | |
| 6,731,978 B2 | 5/2004 | Olson et al. | |
| 6,813,516 B2 | 11/2004 | Ujhelyi et al. | |
| 7,212,855 B1 | 5/2007 | Kroll et al. | |
| 7,225,020 B1 | 5/2007 | Kroll et al. | |
| 7,363,081 B1 | 4/2008 | Kroll et al. | |
| 2004/0049235 A1* | 3/2004 | Deno et al. | 607/9 |

FOREIGN PATENT DOCUMENTS

| | | |
|---|---|---|
| EP | 0253505 A2 | 1/1988 |
| EP | 0993842 A1 | 4/2000 |

OTHER PUBLICATIONS

"International Application Serial No. PCT/US2008/013282, International Search Report mailed Jun. 17, 2009", 5 pgs.
"International Application Serial No. PCT/US2008/013282, Written Opinion mailed Jun. 17, 2009", 8 pgs.
"Confient", Boston Scientific System Guide, (2008), 326 pgs.
"Contak Renewal", Guidant System Guide, (2008), 414 pgs.
"Physician's System Manual Contak CD CHFD", Guidant Physician's System Manual, UK, (1998), 1-147.
"Physician's System Manual Contak CD CRT-D", Guidant Physician's System Manual, US, (2002), 1-176.
"Physician's System Manual Ventak Mini", Guidant Physician's System Manual, UK, (1998), 1-126.
"Physician's System Manual Ventak Mini", Guidant Physician's System Manual, US, (1998), 1-126.
"System Guide: Ventak Prizm, Venrak Prizm HE, Ventak Prizm 2", Guidant System Guide, US, (2008), 1-1—F-22.
"System Guide: Ventak Prizm, Ventak Prizm HE, Ventak Prizm 2", Guidant System Guide, UK, (Nov. 29, 2007), 1-1—E-2.
"Teligen 100", Boston Scientific System Guide, (2008), 328 pgs.
"Vitality 2", Guidant System Guide, (2008), 306 pgs.

* cited by examiner

*Primary Examiner* — George Manuel
(74) *Attorney, Agent, or Firm* — Schwegman, Lundberg & Woessner, P.A.

(57) ABSTRACT

A tachycardia episode can be detected in a subject using a processor, and whether the tachycardia episode is a sustained tachycardia episode can be determined during a period of time. A backup pacing can be provided in response to the detecting tachycardia episode and during the period of time, and a tachycardia therapy can be provided to the subject if the tachycardia episode is determined to be a sustained tachycardia episode.

25 Claims, 3 Drawing Sheets

BACKUP PACING DURING TACHYCARDIA

CROSS-REFERENCE TO RELATED APPLICATION

This application claims the benefit under 35 U.S.C. §119(e) of U.S. Provisional Application No. 61/007,458, filed on Dec. 12, 2007, which is hereby incorporated by reference.

TECHNICAL FIELD

This document pertains generally to implantable medical devices, and more particularly, but not by way of limitation, to biventricular backup pacing during tachycardia.

BACKGROUND

Cardiac rhythm or function management devices can include implantable devices to help maintain heart rhythm or function. Cardiac rhythm or function management devices can include pacers, defibrillators, cardioverters, cardiac resynchronization therapy (CRT), or various combinations of these or other devices. In various examples, cardiac rhythm or function management devices can sense intrinsic heart contractions, deliver pacing pulses to evoke responsive heart contractions, or deliver a shock to interrupt certain arrhythmias. In certain examples, one or more of these functions can help improve a patient's heart rhythm or can help coordinate a spatial nature of a heart contraction, either of which can improve cardiac output of blood to help meet the patient's metabolic need for such cardiac output.

OVERVIEW

A tachycardia episode can be detected in a subject using a processor, and whether the tachycardia episode is a sustained tachycardia episode can be determined during a period of time. A backup pacing can be provided in response to the detecting tachycardia episode and during the period of time, and a tachycardia therapy can be provided to the subject if the tachycardia episode is determined to be a sustained tachycardia episode.

In Example 1, a system includes an implantable medical device and a processor. The implantable medical device can include a right ventricular pacing channel configured to provide a first pacing energy to a right ventricle at a first time or a left ventricular pacing channel configured to provide a second pacing energy to a left ventricle at a second time. The processor can be configured to detect a tachycardia episode, to determine, during a period of time, whether the tachycardia episode is a sustained tachycardia episode, to provide, in response to the detected tachycardia episode and during the period of time, backup pacing using at least one of the right ventricular pacing channel or the left ventricular pacing channel, and to provide, if the tachycardia episode is a sustained tachycardia episode, tachycardia therapy using the implantable medical device.

In Example 2, the processor of Example 1 is optionally configured to receive information indicative of a heart rate and to detect the tachycardia episode using the heart rate information.

In Example 3, the processor of any one or more of Examples 1-2 is optionally configured to detect the tachycardia episode using a first condition including an occurrence of at least a first specified number of fast beats during a second specified number of cardiac cycles.

In Example 4, the first specified number of fast beats of any one or more of Examples 1-3 optionally includes 8 fast beats and the second specified number of cardiac cycles includes 10 cardiac cycles, wherein the fast beat includes a beat having a rate above 100 beats per minute.

In Example 5, the processor of any one or more of Examples 1-4 is optionally configured to provide a first therapy until the tachycardia episode is detected, and to provide, in response to the detected tachycardia episode and if the tachycardia episode is not a sustained tachycardia episode, the backup pacing or the first therapy, wherein the first therapy is different than the tachycardia therapy.

In Example 6, wherein the processor of any one or more of Examples 1-5 is optionally configured to detect a cessation of the tachycardia episode and to provide the first therapy in response to the detected cessation of the tachycardia episode.

In Example 7, the first therapy of any one or more of Examples 1-6 optionally includes at least one of VVI pacing, VDD pacing, or DDD pacing.

In Example 8, the processor of any one or more of Examples 1-7 is optionally configured to receive information indicative of a heart rate, wherein the processor is configured to detect a cessation of the tachycardia episode using the heart rate information.

In Example 9, the processor of any one or more of Examples 1-8 is optionally configured to detect the cessation of the tachycardia episode using a second condition including an occurrence of a third specified number of fast beats or less during a fourth specified number of cardiac cycles.

In Example 10, the third specified number of fast beats of any one or more of Examples 1-9 optionally includes 5 fast beats and the fourth specified number of cardiac cycles of any one or more of Examples 1-9 optionally includes 10 cardiac cycles, wherein the fast beat of any one or more of Examples 1-9 optionally includes a beat having a rate above 100 beats per minute.

In Example 11, the backup pacing of any one or more of Examples 1-10 optionally includes biventricular bradycardia pacing and the tachycardia therapy of any one or more of Examples 1-10 optionally includes antitachycardia pacing (ATP), and wherein the first time of any one or more of Examples 1-10 is optionally different than the second time.

In Example 12, the tachycardia episode of any one or more of Examples 1-11 optionally includes an atrial tachycardia episode, the backup pacing of any one or more of Examples 1-11 optionally includes ventricular backup pacing, and the tachycardia therapy of any one or more of Examples 1-11 optionally includes atrial antitachycardia pacing (ATP).

In Example 13, the backup pacing of any one or more of Examples 1-12 optionally includes biventricular backup pacing and the tachycardia therapy of any one or more of Examples 1-12 optionally includes a shocking energy.

In Example 14, the period of time of any one or more of Examples 1-13 optionally includes a predetermined period of time.

In Example 15, a method includes detecting a tachycardia episode in a subject using processor, determining, during a period of time, whether the tachycardia episode is a sustained tachycardia episode, providing, in response to the detecting the tachycardia episode and during the period of time, backup pacing to at least one of a right ventricle or a left ventricle of the subject, and providing, if the tachycardia episode is determined to be a sustained tachycardia episode, tachycardia therapy to the subject.

In Example 16, the method of Example 15 optionally includes receiving information indicative of a heart rate, wherein the detecting the tachycardia episode of Example 15 optionally includes using the heart rate information.

In Example 17, the detecting the tachycardia episode of any one or more of Examples 15-16 optionally includes detecting a first condition including an occurrence of at least a first specified number of fast beats during a second specified number of cardiac cycles.

In Example 18, the detecting the occurrence of at least the first specified number of fast beats during the second specified number of cardiac cycles of any one or more of Examples 15-17 optionally includes detecting the occurrence of at least 8 fast beats during 10 cardiac cycles, wherein the fast beat includes a beat having a rate above 100 beats per minute, and wherein the detecting the occurrence of at least the first specified number of fast beats of any one or more of Examples 15-17 optionally includes detecting at least the first specified number of beats having a rate above 100 beats per minute.

In Example 19, the method of any one or more of Examples 15-18 optionally includes providing a first therapy until the tachycardia episode is detected, wherein the first therapy is different than the tachycardia therapy, and providing, in response to the detecting the tachycardia episode and if the tachycardia episode is not a sustained tachycardia episode, the backup pacing or the first therapy.

In Example 20, the method of any one or more of Examples 15-19 optionally includes detecting a cessation of the tachycardia episode, and providing the first therapy in response to the detecting the cessation of the tachycardia episode.

In Example 21, the method of any one or more of Examples 15-20 optionally includes receiving information indicative of a heart rate and detecting a cessation of the tachycardia episode using the heart rate information.

In Example 22, the detecting the cessation of the tachycardia episode using a second condition of any one or more of Examples 15-21 optionally includes detecting an occurrence of a third specified number of fast beats or less during a fourth specified number of cardiac cycles.

In Example 23, the detecting the occurrence the third specified number of fast beats or less during the fourth specified number of cardiac cycles of any one or more of Examples 15-22 optionally includes detecting the occurrence of 5 fast beats or less during 10 cardiac cycles, wherein the fast beat of any one or more of Examples 15-22 optionally includes a beat having a rate above 100 beats per minute.

In Example 24, the providing the backup pacing of any one or more of Examples 15-23 optionally includes providing biventricular bradycardia pacing and the tachycardia therapy of any one or more of Examples 15-23 optionally includes providing antitachycardia pacing (ATP), wherein the providing the first pacing energy to the right ventricle at the first time of any one or more of Examples 15-23 optionally includes at the a time different than the second time.

In Example 25, the detecting the tachycardia episode of any one or more of Examples 15-24 optionally includes detecting an atrial tachycardia episode, wherein the providing the backup pacing of any one or more of Examples 15-24 optionally includes providing ventricular backup pacing, and wherein the providing the tachycardia therapy of any one or more of Examples 15-24 optionally includes providing atrial antitachycardia pacing (ATP).

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Generally, tachycardia refers to a fast cardiac rhythm, e.g., a heart rate greater than 100 beats per minute, etc. Various types of tachycardia include ventricular tachycardia, supraventricular tachycardia, or other types of tachycardia. Ventricular tachycardia can include a tachycardia that originates in the ventricles having the potential to degrade into a ventricular fibrillation, or an uncoordinated contraction of the ventricles. A ventricular fibrillation can cause cardiac arrest and sudden cardiac arrest. A ventricular tachycardia can be classified in numerous ways, including based upon its morphology (e.g., a monomorphic ventricular tachycardia where the morphology of the cardiac rhythm is similar for each cardiac cycle or a polymorphic ventricular tachycardia where the morphology of the cardiac rhythm includes variations among cardiac cycles), its duration (e.g., a non-sustained ventricular tachycardia that self terminates within a certain time period, such as 30 seconds, or a sustained ventricular tachycardia that survives the certain time period, such as 30 seconds), or its symptoms (e.g., pulseless ventricular tachycardia includes no effective cardiac output).

In an example, dual chamber pacing includes pacing where energy is delivered to both the atrium and the ventricle. An atrioventricular (AV) delay interval, as used herein, refers to the interval between an atrial event (e.g., an atrial pace or an atrial sense, usually the right atrium) and a first ventricular pace to one of the ventricles (e.g., a right ventricle). The AV delay interval can be the same or different depending upon whether it is initiated by an atrial sense or an atrial pace (e.g., in atrial tracking mode or AV sequential pacing mode, respectively). Biventricular pacing includes pacing both the left ventricle and the right ventricle. The biventricular offset (BVO) interval, as used herein, refers to the interval between the first ventricular pace and a second ventricular pace to the other ventricle (e.g., the left ventricle) during the same cardiac cycle. One approach to biventricular pacing includes specifying an AV delay interval and a BVO interval. Another approach to biventricular pacing includes specifying a separate AV delay interval for each ventricle, which can be designated as AVDR for the right ventricle and AVDL for the left ventricle. Generally, for subjects having intact or normally functioning AV conduction pathways, the later-paced ventricle will be paced, if at all, close to the time at which that ventricle is intrinsically activated, such as to achieve an optimal or desired preloading. In subjects having normal AV conduction, the optimal or desired AVD and BVO intervals are thus related to both the intrinsic atrioventricular interval and the amount of pre-excitation time needed for one ventricle relative to the other (e.g., the extent of the ventricular conduction deficit).

Figure 1:
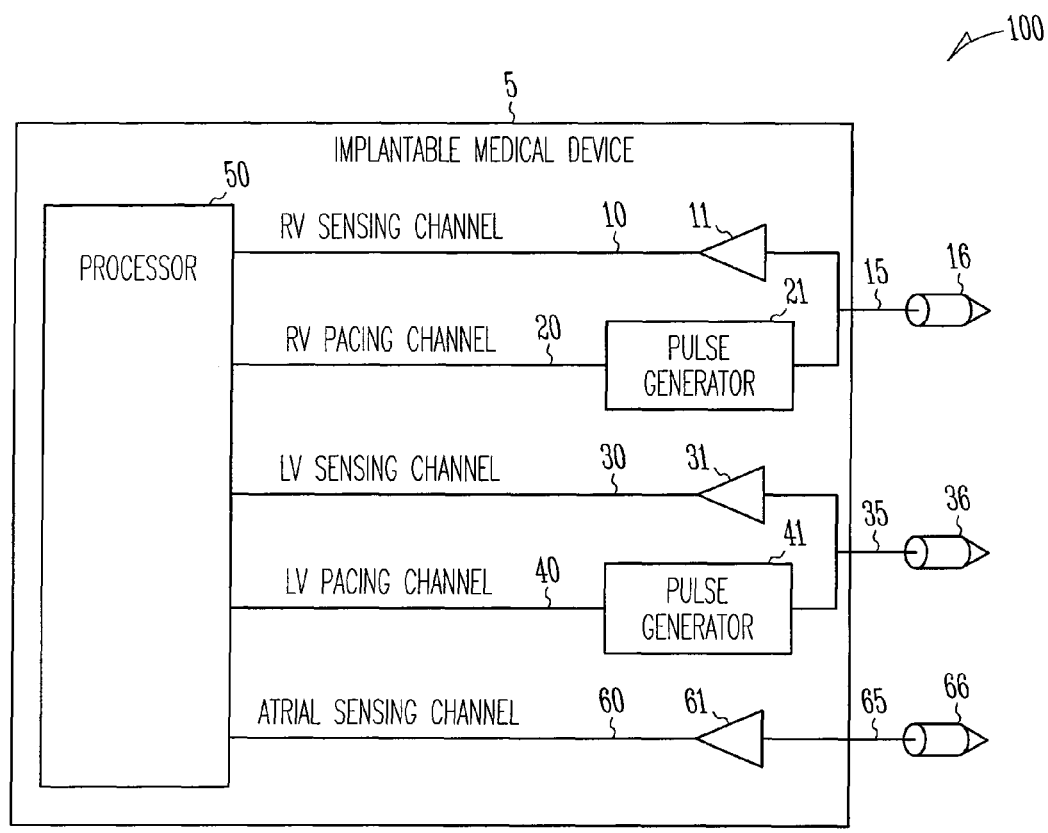
FIGS. 1 and 2 illustrate generally examples of systems or portions of a system for delivering cardiac therapy.

FIG. 1 illustrates generally an example of a system 100 for delivering cardiac therapy. In an example, the system 100 can include an implantable medical device (IMD) 5 having a processor 50, a right ventricular sensing channel 10, a right ventricular pacing channel 20, a left ventricular sensing channel 30, a left ventricular pacing channel 40, and an atrial sensing channel 60. The atrial sensing channel 60 can include at least one of a right atrial sensing channel or a left atrial sensing channel. In other examples, the IMD 5 can include a combination of at least one of the a right ventricular sensing channel 10, the right ventricular pacing channel 20, the left ventricular sensing channel 30, the left ventricular pacing channel 40, or the atrial sensing channel 60.

In certain examples, the right ventricular sensing channel 10 can include a sense amplifier 11, the left ventricular sensing channel 30 can include a sense amplifier 31, the right ventricle pacing channel 20 can include a pulse generator 21, the left ventricular pacing channel 40 can include a pulse generator 41, and the atrial sensing channel 60 can include a sense amplifier 61. In other examples, the right ventricular sensing channel 10 or the right ventricular pacing channel 20 can be coupled to an electrode 16 disposed on a lead 15 or elsewhere, the left ventricular sensing channel 30 or the left ventricular pacing channels 40 can be coupled to an electrode 36 disposed on a lead 35 or elsewhere, or the atrial sensing channel 60 can be coupled to an electrode 66 disposed on a lead 65 or elsewhere.

In certain examples, the lead 15 can be configured to electrically couple the sense amplifier 11 or the pulse generator 21 to the electrode 16, which can be configured to be located in a right ventricle, such as in the septal region, the free wall region, or another region of the right ventricle. Similarly, the lead 35 can be configured to electrically couple the sense amplifier 31 or the pulse generator 41 to the electrode 36, which can be configured to be located in, on, or near a left ventricle, such as in the septal region, the free wall region, or another region of the left ventricle or in the coronary vasculature. Further, the lead 65 can be configured to electrically couple the sense amplifier 61 to the electrode 66, which can be configured to be located in at least one of a right atrium or a left atrium of the subject 101.

In certain examples, the implantable medical device 5 can include one or more other pacing or sensing channels, such as an internal thoracic pacing or sensing channel configured to couple the processor 50 to an internal thoracic location external to the heart (e.g., through one or more leads, electrodes, pulse generators, or sense amplifiers). In an example, the internal thoracic pacing or sensing channel can be configured to send or receive information to or from a housing can electrode, located on the exterior housing of an implantable medical device located in the internal thoracic location external to the heart.

In the example of FIG. 1, the processor 50 can be an implantable component, an external component, or a combination or permutation of an implantable processor and an external processor. In an example, if at least a portion of the processor 50 includes an external processor, then the processor 50 can be configured to be communicatively coupled (such as via telemetry, RF, or other communication protocol) with the remaining implantable components (such as the sense amplifier 11, 31, the pulse generator 21, 41, the lead 15, 35, or the electrode 16, 36). In an example, the implantable processor can be configured to have reduced or minimal functionality or power consumption. In certain examples, it can be advantageous for the processor 50 to include an external processor for computing complex operations, such as to compute an AV delay interval. In other examples, the external processor can include an external device that can be either local or remote. In an example, the processor 50 can include a microcontroller, a microprocessor, a logic circuit, or other processor.

Figure 2:
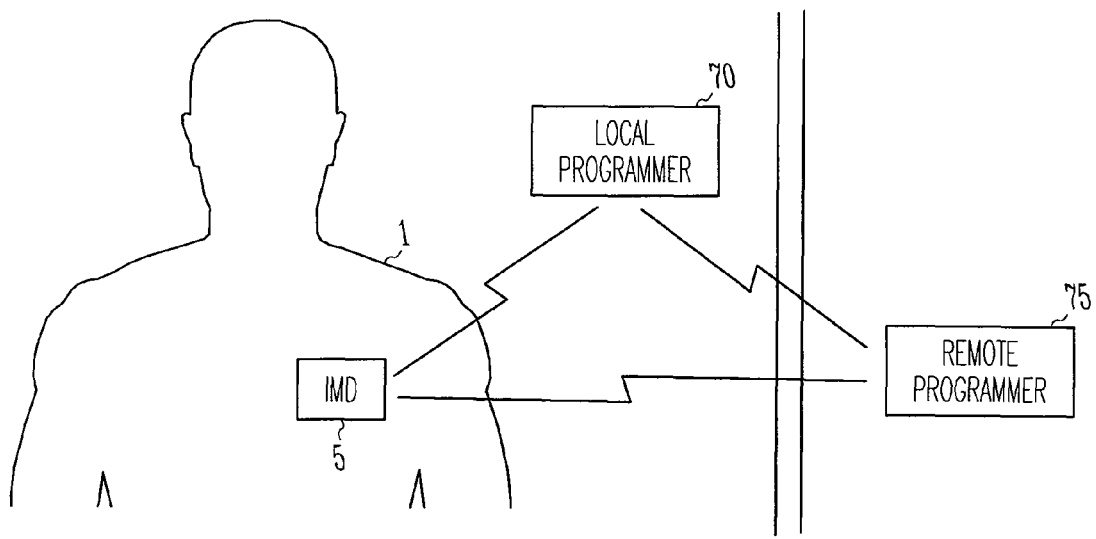

FIG. 2 illustrates generally an example of a portion of a system 200 including an IMD 5 configured to be implanted in a subject 101. The system 200 can include at least one of a local programmer 70 or a remote programmer 75. Both the local programmer 70 and the remote programmer 75 are external components. In an example, the local programmer 70 can include a hand-held programmer or other programmer capable of being positioned in communication proximity to the processor 50. The proximity range between the processor 50 and the local programmer 70 can vary depending upon the type of data communication and is bound by the physical constraints of the communication type. In an example, the remote programmer 75 can include any programmer configured to communicate with the IMD 5 either directly or indirectly (such as through another device, e.g., a router, the local programmer 70, etc.). In various examples, the remote programmer 75 can be configured to communicate with or store information from a plurality of implanted or external devices, and the remote programmer 75 can be configured to be located a long distance from the subject 1.

In an example, the local programmer 70 or the remote programmer 75 can be configured to send information to or receive information from the IMD 5. The information can include programming information, subject data, device data, or other instructions, alerts, or other information. Further, the local programmer 70 or the remote programmer 75 can be configured to communicate the sent or received information to a user or physician, such as by sending an alert via email of the status of the subject 1 or the system components.

Biventricular Backup Pacing

Figure 3:
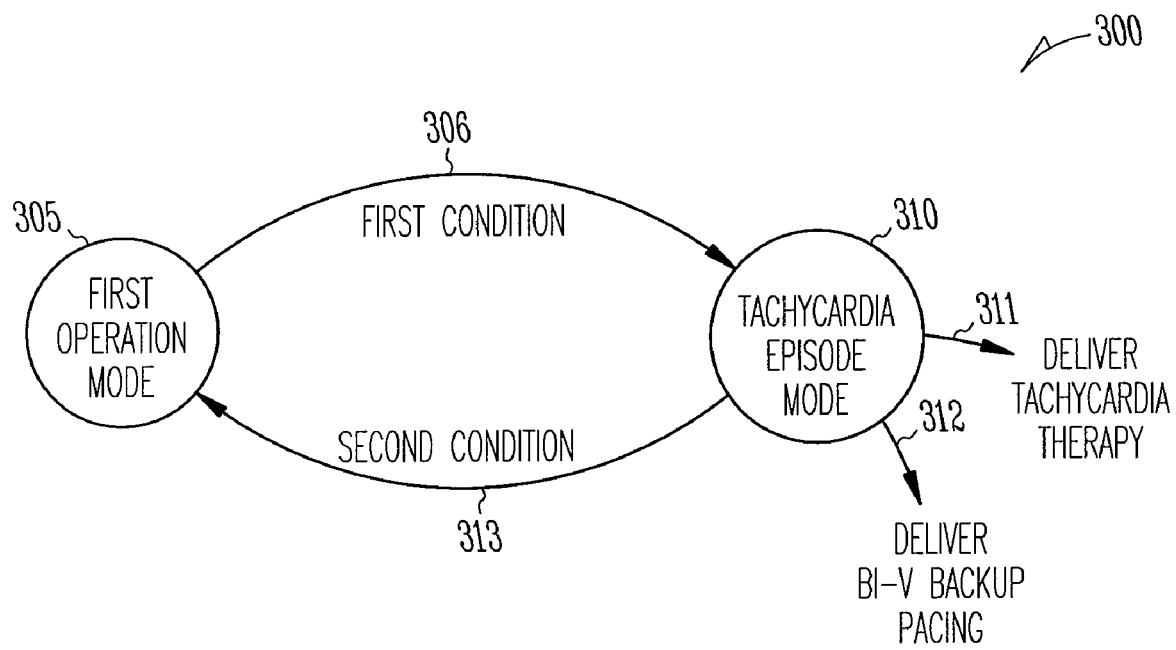
FIG. 3 illustrates generally an example of a state diagram illustrating switching between a first or normal operation mode and a tachycardia episode mode.

FIG. 3 illustrates generally an example of a state diagram 300 illustrating switching between a first (e.g., normal) operation mode 305 and a tachycardia episode mode 310. In certain examples, the first operation mode 305 can include various types of cardiac pacing, cardioversion, defibrillation, or other electrical or other cardiac therapy. In various examples, first operation mode 305 can include single chamber pacing, dual chamber pacing, biventricular pacing, or other pacing types depending on the physiological data or condition of the subject, and the first operation mode 305 can include various pacing modes, including VVI, AAI, VDD, DDD, or other pacing modes depending on the physiological data or condition of the subject as well as the type of pacing. In certain examples, the first operation mode 305 can utilize one or more of the pacing or sensing channels of the implantable medical device 5 to implement one or more various types of pacing, cardioversion, defibrillation, or other electrical or other therapy.

In the example of FIG. 3, during the first operation mode 305, a first condition 306 (e.g., a fast beats/b cardiac cycles, 8 fast beats/10 cardiac cycles, etc., where fast beats can include a rate consistent with a tachycardia episode, such as 100 beats per minute, etc.) satisfies the entry criteria into the tachycardia episode mode 310. In an example, the fast beats and the cardiac cycles can be detected using information from one or more of the pacing or sensing channels of the implantable medical device 5, or one or more other sensing or receiving channels or sources of information.

In an example, one or more other tachycardia detection algorithms can be used as entry criteria to tachycardia episode mode 310. In an example, the tachycardia episode mode 310 can deliver tachycardia therapy 311 and deliver biventricular backup pacing 312. The deliver tachycardia therapy 311 function can include delivering an electrical energy to the heart, such as a cardioversion energy, a defibrillation energy, or a pacing energy (e.g., antitachycardia pacing (ATP), such as ventricular ATP or atrial ATP), configured to cease the tachycardia and return the heart back to a normal or a manageable cardiac rhythm.

In an example, the deliver biventricular backup pacing 312 function can include delivering a pacing to the heart (e.g., to at least one of the atria or the ventricles) during the detected tachycardia different than the tachycardia therapy. In an example, the backup pacing can include bradycardia pacing, or pacing the heart to sustain at least a minimum rate of cardiac pulses during the tachycardia episode. In an example, the backup bradycardia pacing during tachycardia can include biventricular bradycardia pacing having independent control of the timing or energy of pacing of each ventricle. In certain examples, such independent control of pacing each ventricle can be advantageous, for example, to provide an increased cardiac output or hemodynamic performance during the tachycardia. In an example, the biventricular bradycardia backup pacing can include a bradycardia pacing having at least one of an atrioventricular (AV) delay offset or a biventricular offset (BVO) interval.

In an example, during the tachycardia episode mode 310, a second condition 313 (e.g., c fast beats/d cardiac cycles, 5 fast beats/10 cardiac cycles, etc., where fast beats can include a rate consistent with a tachycardia episode, such as 100 beats per minute, etc.) satisfies the entry criteria back into the first operation mode 305. In other examples, other first or normal operation detection algorithms can be used as entry criteria back into the first operation mode 305.

Figure 4:
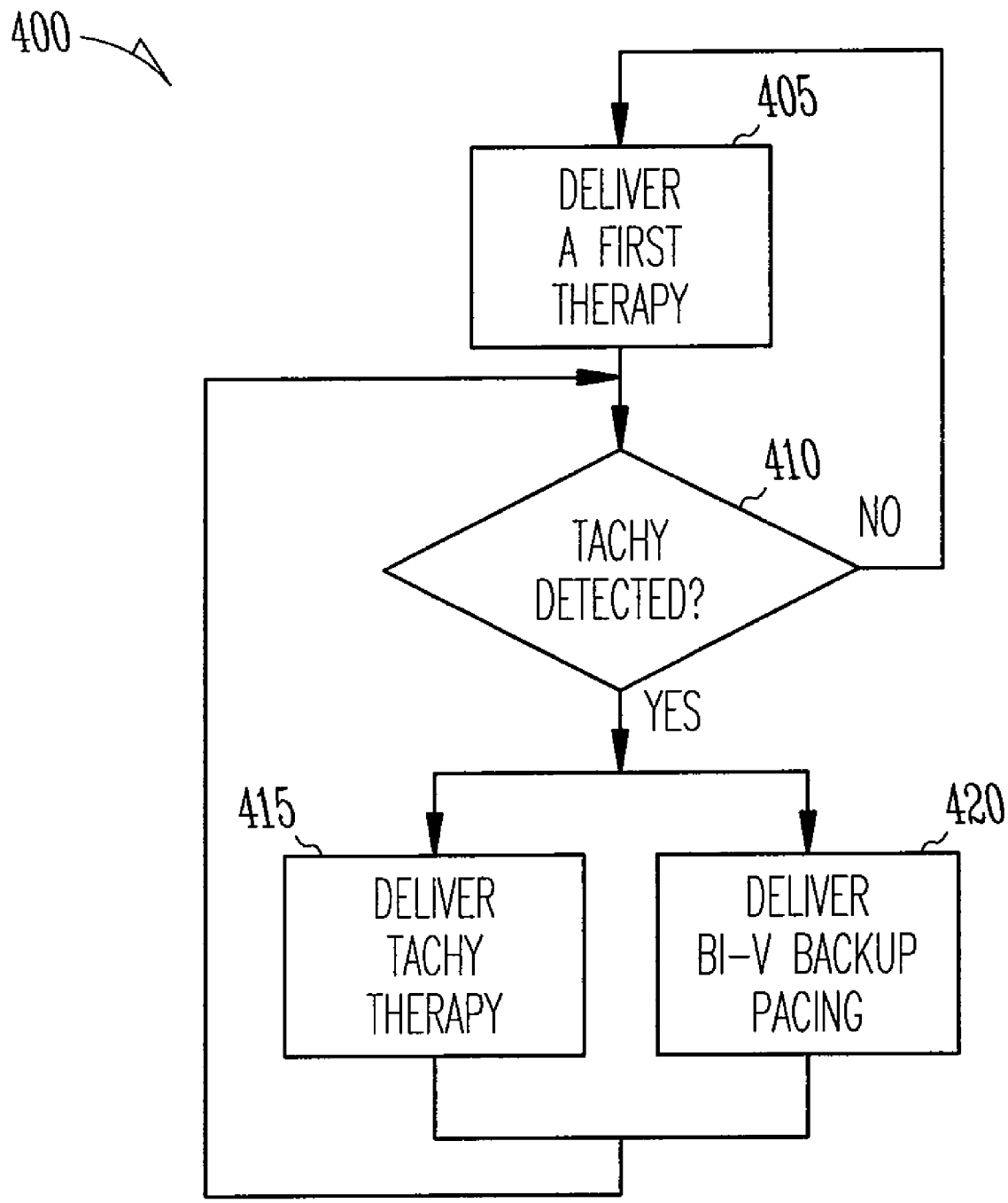
FIG. 4 illustrates generally an example of a method of delivering biventricular backup pacing during a detected tachycardia.

FIG. 4 illustrates generally an example of a method 400 of delivering biventricular backup pacing during a detected tachycardia.

At 405, a first therapy is delivered, such as by using IMD 5.

At 410, a tachycardia is detected. If, at 410, a tachycardia is detected, then at 415, a tachycardia therapy is delivered and, at 420, a biventricular backup pacing is delivered. If, at 410, a tachycardia is not detected, then process flow returns to 405, and the first therapy is delivered.

In an example, if, at 410, a tachycardia is detected, then, at 420, the tachycardia therapy can be delayed for an interval following the detection of the tachycardia (e.g., delayed to determine whether the tachycardia is a sustained tachycardia or a non-sustained tachycardia). The delay interval can include a programmable interval set by a clinician (e.g., 2.5 seconds, 15 seconds, 30 seconds, etc.). In an example, if the tachycardia episode terminates during the delay interval (e.g., a non-sustained tachycardia) then the tachycardia therapy is not delivered. In certain examples, once the tachycardia is detected, the biventricular backup pacing can be delivered, including during the delay interval.

In an example, the tachycardia therapy and the biventricular backup pacing can be delivered concurrently. In certain examples, the tachycardia therapy, e.g., a shock, can be delivered before the biventricular backup pacing is delivered, while the biventricular backup pacing is being delivered, or after the biventricular backup pacing is delivered. In other examples, the biventricular backup pacing can be delivered before the tachycardia therapy is delivered, while the tachycardia therapy is being delivered, or after the tachycardia therapy is delivered.

In an example, if, at 415, the delivered tachycardia therapy includes ventricular ATP (or biventricular ATP), then, at 420, the biventricular backup pacing can be delivered before the tachycardia therapy is delivered, or the biventricular backup pacing can be delivered after the tachycardia therapy is delivered. In an example, if, at 415, the delivered tachycardia therapy includes atrial ATP, then, at 420, the biventricular backup pacing can be delivered during before the tachycardia therapy is delivered, the biventricular backup pacing can be delivered while the tachycardia therapy is delivered, or the biventricular backup pacing can be delivered after the tachycardia therapy is delivered.

In an example, if, at 415, the delivered tachycardia therapy includes a cardioversion energy or a defibrillation energy (e.g., a shocking energy), then, at 420, the biventricular backup pacing can be delivered before the tachycardia therapy is delivered, or the biventricular backup pacing can be delivered after the tachycardia therapy is delivered.

In an example, at 420, the delivery of the biventricular backup pacing can include delivering independently controlled biventricular pacing therapy (e.g., including at least one of an AV delay interval or a BVO interval) configured to optimize the bradycardia pacing.

In an example, if, at 410, an atrial tachycardia episode (or, in certain examples, a supraventricular tachycardia (SVT)) is detected, then, at 415, a ventricular backup pacing can be delivered, and, at 420, atrial ATP can be delivered.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
an implantable medical device including:
a right ventricular pacing channel configured to provide a first pacing energy to a right ventricle; and
a left ventricular pacing channel configured to provide a second pacing energy to a left ventricle; and
a processor configured to detect a tachycardia episode, to determine, during a period of time, whether the tachycardia episode is a sustained tachycardia episode, to provide, in response to the detected tachycardia episode and during the period of time, bi-ventricular backup pacing using the right ventricular pacing channel and the left ventricular pacing channel, and to provide, if the tachycardia episode is a sustained tachycardia episode, tachycardia therapy using the implantable medical device.

2. The system of claim 1, wherein the processor is configured to receive information indicative of a heart rate; and
wherein the processor is configured to detect the tachycardia episode using the heart rate information.

3. The system of claim 2, wherein the processor is configured to detect the tachycardia episode using a first condition including an occurrence of at least a first specified number of fast beats during a second specified number of cardiac cycles.

4. The system of claim 3, wherein the first specified number of fast beats includes 8 fast beats and the second specified number of cardiac cycles includes 10 cardiac cycles; and
wherein the fast beat includes a beat having a rate above 100 beats per minute.

5. The system of claim 1, wherein the processor is configured to provide a first therapy until the tachycardia episode is detected, and to provide, in response to the detected tachycardia episode and if the tachycardia episode is not a sustained tachycardia episode, the backup pacing or the first therapy, wherein the first therapy is different than the tachycardia therapy.

6. The system of claim 5, wherein the processor is configured to detect a cessation of the tachycardia episode and to provide the first therapy in response to the detected cessation of the tachycardia episode.

7. The system of claim 5, wherein the first therapy includes at least one of VVI pacing, VDD pacing, or DDD pacing.

8. The system of claim 1, wherein the processor is configured to receive information indicative of a heart rate; and
wherein the processor is configured to detect a cessation of the tachycardia episode using the heart rate information.

9. The system of claim 8, wherein the processor is configured to detect the cessation of the tachycardia episode using a second condition including an occurrence of a third specified number of fast beats or less during a fourth specified number of cardiac cycles.

10. The system of claim 9, wherein the third specified number of fast beats includes 5 fast beats and the fourth specified number of cardiac cycles includes 10 cardiac cycles; and
wherein the fast beat includes a beat having a rate above 100 beats per minute.

11. The system of claim 1, wherein the backup pacing includes biventricular bradycardia pacing and the tachycardia therapy includes antitachycardia pacing (ATP); and
wherein the first time is different than the second time.

12. The system of claim 1, wherein the tachycardia episode includes an atrial tachycardia episode, the backup pacing includes ventricular backup pacing, and the tachycardia therapy includes atrial antitachycardia pacing (ATP).

13. The system of claim 1, wherein the backup pacing includes biventricular backup pacing and the tachycardia therapy includes a shocking energy.

14. The system of claim 1, wherein the period of time includes a predetermined period of time.

15. A method comprising:
detecting a tachycardia episode in a subject using processor;
determining, during a period of time, whether the tachycardia episode is a sustained tachycardia episode;
providing, in response to the detecting the tachycardia episode and during the period of time, bi-ventricular backup pacing to a right ventricle and a left ventricle of the subject; and
providing, if the tachycardia episode is determined to be a sustained tachycardia episode, tachycardia therapy to the subject.

16. The method of claim 15, including receiving information indicative of a heart rate; and
wherein the detecting the tachycardia episode includes using the heart rate information.

17. The method of claim 16, wherein the detecting the tachycardia episode includes detecting a first condition including an occurrence of at least a first specified number of fast beats during a second specified number of cardiac cycles.

18. The method of claim 17, wherein the detecting the occurrence of at least the first specified number of fast beats during the second specified number of cardiac cycles includes detecting the occurrence of at least 8 fast beats during 10 cardiac cycles, wherein the fast beat includes a beat having a rate above 100 beats per minute; and
wherein the detecting the occurrence of at least the first specified number of fast beats includes detecting at least the first specified number of beats having a rate above 100 beats per minute.

19. The method of claim 15, including:
providing a first therapy until the tachycardia episode is detected, wherein the first therapy is different than the tachycardia therapy; and
providing, in response to the detecting the tachycardia episode and if the tachycardia episode is not a sustained tachycardia episode, the backup pacing or the first therapy.

20. The method of claim 19, including:
detecting a cessation of the tachycardia episode; and
providing the first therapy in response to the detecting the cessation of the tachycardia episode.

21. The method of claim 15, including receiving information indicative of a heart rate and detecting a cessation of the tachycardia episode using the heart rate information.

22. The method of claim 21, wherein the detecting the cessation of the tachycardia episode using a second condition includes detecting an occurrence of a third specified number of fast beats or less during a fourth specified number of cardiac cycles.

23. The method of claim 22, wherein the detecting the occurrence the third specified number of fast beats or less during the fourth specified number of cardiac cycles includes detecting the occurrence of 5 fast beats or less during 10 cardiac cycles, wherein the fast beat includes a beat having a rate above 100 beats per minute.

24. The method of claim 15, wherein the providing the backup pacing includes providing biventricular bradycardia pacing and the providing the tachycardia therapy includes providing antitachycardia pacing (ATP); and wherein the providing the first pacing energy to the right ventricle at the first time includes at a time different than the second time.

25. The method of claim 15, wherein the detecting the tachycardia episode includes detecting an atrial tachycardia episode, wherein the providing the backup pacing includes providing ventricular backup pacing, and wherein the providing the tachycardia therapy includes providing atrial antitachycardia pacing (ATP).

* * * * *